United States Patent [19]

Rothfuss

[11] Patent Number: 4,805,823
[45] Date of Patent: Feb. 21, 1989

[54] POCKET CONFIGURATION FOR INTERNAL ORGAN STAPLERS

[75] Inventor: Robert G. Rothfuss, Bellevue, Ky.

[73] Assignee: Ethicon, Inc., Somerville, N.J.

[21] Appl. No.: 169,666

[22] Filed: Mar. 18, 1988

[51] Int. Cl.⁴ .......................................... A61B 17/00
[52] U.S. Cl. ............................... 227/19; 227/139; 227/156; 227/DIG. 1
[58] Field of Search ............... 227/19, 107, 156, 119, 227/139, DIG. 1; 128/334 R, 334 C, 335

[56] References Cited

U.S. PATENT DOCUMENTS 4,589,582 5/1986 Bilotti .................................. 227/19

Primary Examiner—Donald R. Schran
Assistant Examiner—James L. Wolfe
Attorney, Agent, or Firm—Paul A. Coletti

[57] ABSTRACT

A guiding pocket for driving staples is described, in which a first set of parallel sides helps form the opening for the guiding pockets. These parallel sides are connected to tapered sides, which are in turn connected to a second pair of parallel sides, creating a hexagonal shaped pocket. The resultant pocket configuration possesses self-centering features, which in turn reduces jamming and misformed staples and allows for simpler manufacturing and inspection.

8 Claims, 2 Drawing Sheets

POCKET CONFIGURATION FOR INTERNAL ORGAN STAPLERS

FIELD OF THE INVENTION

The present invention relates to surgical staplers. More particularly, the present invention relates to improved pockets used to guide staples as they are driven to the anvil in a surgical stapler.

BACKGROUND OF THE INVENTION

Presently, in surgical staplers, staples pass through guiding pockets by means of a driver to a forming surface. These pockets are generally long, rectangular channels through which pass the staples in an unformed state. A pocket conforms to the generally rectangular cross-sectional shape of the staple driver. When the staple passes through the pocket by force of the staple driver, it is guided down the pocket channel and onto the anvil of the stapler. It is at the anvil where the staple driver forms the staple. The staple driver remains in the pocket channel, during forming of the staple. The gap between the driver and the anvil is set so that generally most of the gap is filled by the staple.

Generally, the presently used pockets have a rectangular shape. That is, there are generally a first pair of parallel sides which are formed along the length of the unformed staple. This first pair of parallel sides is met by a second pair of parallel sides at right angles. This second pair of parallel sides generally corresponds to the width of the staple and staple driver.

However, when the staple passes through the generally rectangular-shaped pocket, it may cause the stapler to jam. This happens when the staple has been loaded in the pocket at an angle to the generally parallel sides of the pocket. When placed at this angle, the staple can be forced by the driver until the staple becomes wedged in the staple forming pocket or is misformed on the anvil.

The presently shaped staple pockets have other drawbacks, both in method of manufacture and in ease of operation. Because these staple pockets have the potential to be misloaded or to jam, it is generally desired to keep the tolerances between the forming pockets and the staples very close. This minimizes the chances of the staple being loaded and guided in the pocket in any other way except in a properly aligned fashion. However, when this is done, it is difficult to consistently manufacture the staple pockets to such close tolerances. This is very costly and time consuming. In addition, it is much more difficult to inspect the staple pockets to determine whether they have been maintained at the proper tolerances. Of course, if the tolerances are kept close, there is also the possibility that the staple pockets are manufactured to be too small for the staples.

Finally, one other disadvantage of the presently formed staple pockets is that they are difficult to load with staples. This is true because the staples that are misloaded tend to become jammed in the pockets, usually during contact with the staple driver. Because it is not plainly determinable whether the stables will jam within the pockets, the pockets frequently will retain some of the staples.

SUMMARY OF THE INVENTION

The present invention overcomes these and other difficulties arising in presently formed staple driving pockets by creating a self-centering pocket which is able to maintain the staples in proper alignment. This pocket is also easy to measure and manufacture. Essentially, the pocket comprises a pair of parallel sides each connected to a pair of tapered sides. This pair of tapered sides culminates at a second pair of parallel sides, situated at right angles to the first pair of parallel sides. Thus, the improved guiding pocket takes of a generally hexagonal shape. It is this hexagonal shape which allows the staple to center itself inside the pocket. That is, when the staple is loaded into the channel, the staple is encouraged to move toward an aligned position, along the axis of the first pair of parallel sides.

These and other aspects of the preferred embodiment of the present invention will be better understood from the accompanying detailed description of the drawings as well as the detailed description in which:

DETAILED DESCRIPTION OF THE DRAWINGS

FIGS. 1, 2, and 3 are bottom views of typical improved staple pockets;

DETAILED DESCRIPTION

As seen in FIGS. 1a-3a, the prior art staple guiding pockets are configured to have generally close tolerances. This is due mostly to the shape of these guiding pockets. Generally these guiding pockets will be formed so that the staple can be loaded inside the guiding pocket in one fashion. If these close tolerances are kept up to specification, then the guiding pockets are able to accurately hold and guide the staples. However, generally the guiding pockets will be formed with a wider tolerance than the size of the staple. When this occurs, it is possible for the staple to be wedged inside the guiding pocket. When this occurs, of course, it delays use of the stapler because the staple must be evacuated from the pocket.

Figure 1:
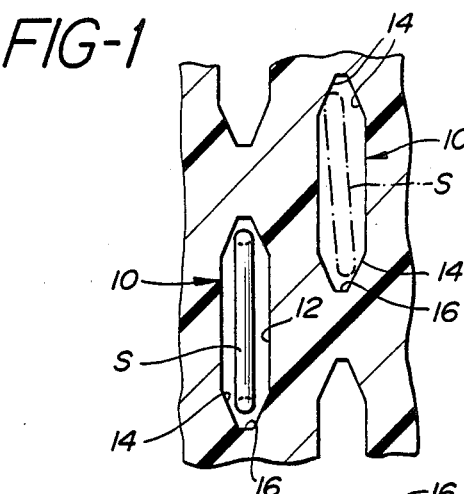
FIGS. 1a, 2a and 3a are bottom views of prior art embodiments of staple pockets.
Figure 1A:
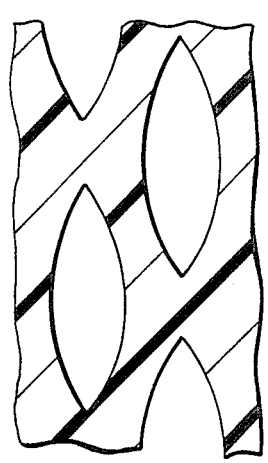
Figure 2:
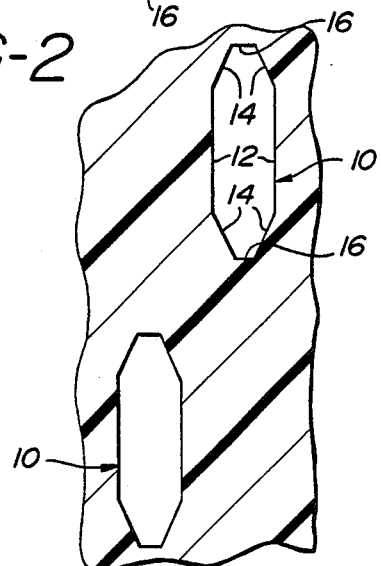
Figure 2A:
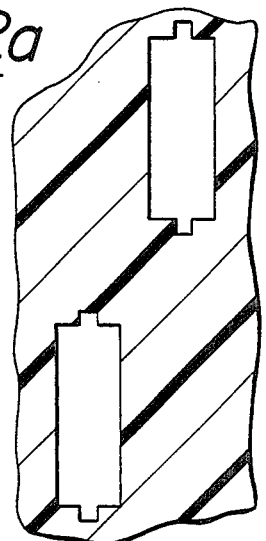
Figure 3:
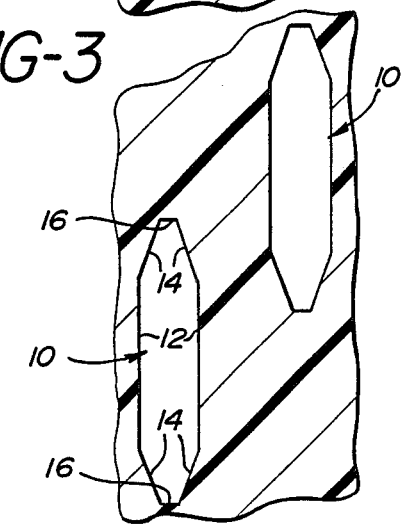
Figure 3A:
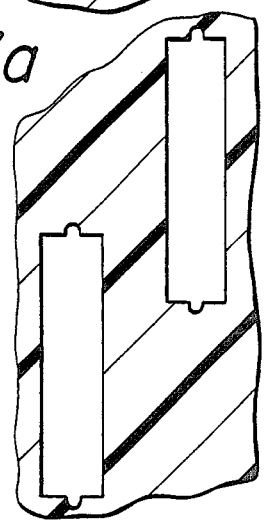
Figure 4:
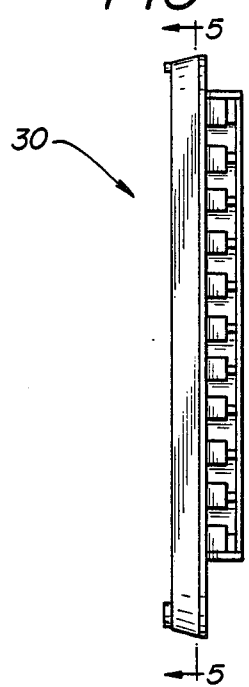
FIG. 4 is an elevation view of the staple guiding pockets of the present invention in relationship to staple drivers.
Figure 5:
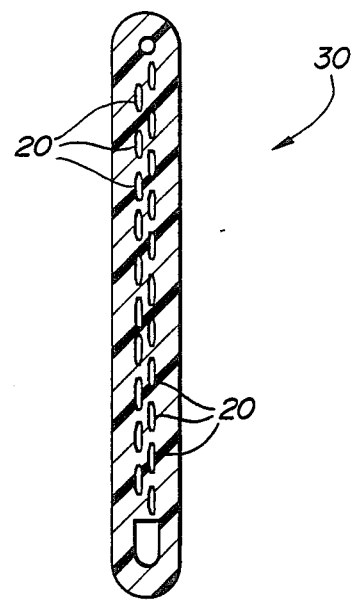
FIG. 5 is a sectional view of a preferred embodiment of the staple guiding pocket of the present invention as taken along lines 5—5 of FIG. 4.
Figure 6:
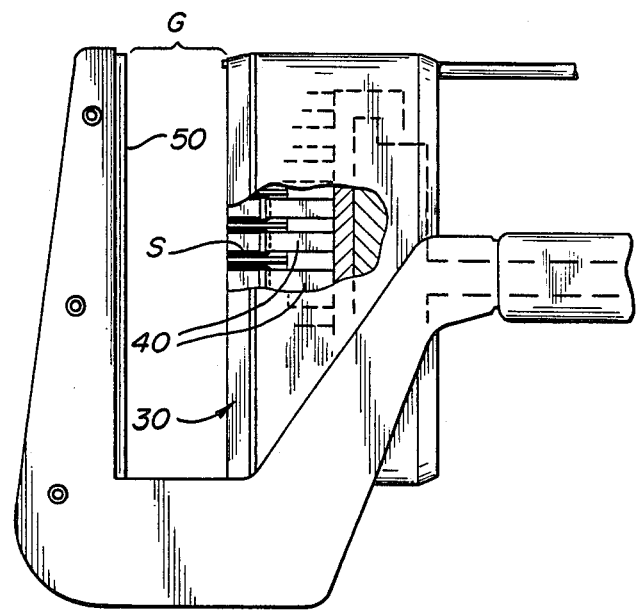
FIG. 6 is a partial sectional view of the staple guiding pockets of the present invention as used in a surgical stapler.

The present invention, as seen in FIGS. 1-3, overcomes this difficulty. The new pocket 10 has a pair of first parallel sides 12. Each of these parallel sides 12 has two ends. These ends are connected to a pair of tapered sides 14. These tapered sides 14 generally extend from beyond first parallel sides 12 for the length of the staple, to a pair of second parallel sides 16. These second parallel sides 16 connect to both pairs of tapered sides 14. As seen in FIGS. 4-6, these pockets can be used in staple cartridge 30 containing pockets 20. The drivers 40 pass from the staple cartridge 30 so that the staples pass through the pockets 20 onto the anvil 50 of the stapler. The pockets 20 are placed strategically to create the staple forming gap G which will cause the staples to be formed to a certain height in order to close the skin to be stapled.

The resultant pocket of the present invention allows the staple to be self-centering. Return to FIGS. 1-3, should the staple become placed in the pocket 10 along the tapered sides 14 of the pocket 10, as seen in phantom, FIG. 1, the staple 10 will necessarily rotate toward the appropriate axes so that it fits into a guiding pocket 10 correctly, as demonstrated in the adjoining pocket of FIG. 1. This is due to the geometry of the pocket of the present invention. The staple slides against the sides of the guiding pocket wall so that it becomes properly aligned. This feature of the pocket is a substantial improvement over the presently practiced pocket. With the new shape of the pocket, jamming is reduced, as well as misforming of staples. Stapling can occur more reliably. This also allows for simpler manufacturing and inspection of staple cartridges.

Also, the preferred embodiment of the present invention makes measurement of the pocket size much easier. These pockets can accommodate staple wire diameters generally in the range from 0.008 to 0.011 inches, although these are not critical dimensions. Of course, the length of the first parallel sides and tapered sides may have any dimension required to fit the surgical staple. In this instance, the angle between the first parallel sides and the tapered sides is maintained at about 22.5°. This is the optimal angle to insure the self aligning features of the present invention for a range of different staple wire diameters.

The present invention, therefore, can be used in all types of internal organ surgical staplers, especially the RL 30V, PLC-50, and any 60 millimeter cartridges made by the assignee of the present invention.

While this particular invention has been described in connection with the presently preferred embodiment, it will be understood that its scope is to include any modifications to the invention which cause substantially similar functions to be performed in substantially the same way. Furthermore, it is recognized that the invention is described in connection with the attached claims in which:

What is claimed is:

1. In a stapler having pockets through which pass staple drivers adapted to drive unformed staples, each said pocket generally conforming to the shape of one of said unformed staples, said pockets permitting said drivers to position said unformed staples on anvils for forming said staples, one of said pockets having first parallel sides generally corresponding to the length of said unformed staples, said first parallel sides connected by second parallel sides to form said pocket, said second parallel sides generally conforming to the width of said unformed staples, the improvement comprising the addition of a tapered side to each end of each first parallel side, each said tapered side diagonally approaching one of said second parallel sides, the resulting pocket formed with a generally hexagonal shape, wherein staples within said pocket become self-aligning.

2. In the stapler having pockets as in claim 1, the improvement further comprising forming said tapered sides at angles in the range of about 22.5°.

3. In the stapler having pockets as in claim 1, the improvement further comprising said second parallel sides having a length of about 0.008".

4. In the stapler having pockets as in claim 1, the improvement further comprising said second parallel sides having a length of about 0.011".

5. In a staple cartridge, a pocket for emplacement of staples, said pocket having a pair of first parallel sides, each of said first parallel sides connected to a pair of tapered sides, said tapered sides displaced angularly to said pair of first parallel sides, each of said tapered sides connected at its opposite end to a pair of second parallel sides, said resultant pocket forming a generally hexagonal shape.

6. The pocket of claim 5, wherein said generally hexagonal shape of said pocket is bored through a driving chamber in a stapler, wherein said staples may pass through said pocket by force of a staple driver.

7. The pocket of claim 5, wherein said tapered sides are angularly displaced from said first pair of parallel sides at an angle in the range of about 22.5°.

8. The pocket of claim 5, wherein said second pair of parallel sides have a length in the range of about 0.008" to about 0.011".

* * * * *